United States Patent [19]

Klein

[11] 4,206,755

[45] Jun. 10, 1980

[54] METHOD AND APPARATUS FOR THE CONTROL AND REGULATION OF GLYCEMIA

[75] Inventor: Jean-Claude Klein, Avon, France

[73] Assignee: Association pour la Recherche et le Developpement des Methodes et Processus Industriels A.R.M.I.N.E.S., Paris, France

[21] Appl. No.: 897,388

[22] Filed: Apr. 18, 1978

[30] Foreign Application Priority Data

Apr. 21, 1977 [FR] France .................................. 77 12054

[51] Int. Cl.² .............................................. A61M 5/00
[52] U.S. Cl. .................................. 128/214 E; 128/637
[58] Field of Search .............. 128/2 E, 2 G, 2 P, 2 R; 692/2.1 E; 693/213, 214 E, 260; 73/194 E

[56] References Cited

PUBLICATIONS

Albisser et al., "Diabetes," vol. 23, May 1974, pp. 389–396.
Kline et al., "Medical Research Engineering," 2nd Qtr. 1968, pp. 10–16.
Kalish, "American Journal of Medical Electronics," vol. 3, pp. 82–86.

Primary Examiner—William E. Kamm
Attorney, Agent, or Firm—Ostrolenk, Faber, Gerb & Soffen

[57] ABSTRACT

The invention relates to the control and regulation of glycemia (that is the glucose rate in blood) for diabetic patients. The device comprises means for sampling the total blood of a diabetic patient 2, means 9 for determining the glycemia of the blood, an electronic unit 11 providing, as a function of the indications at 9, the operation of pumps 15 apable of injecting insulin or 16 capable of injecting glucose. There are also provided recording means for the glycemia 14 and a sound alarm.

6 Claims, 4 Drawing Figures

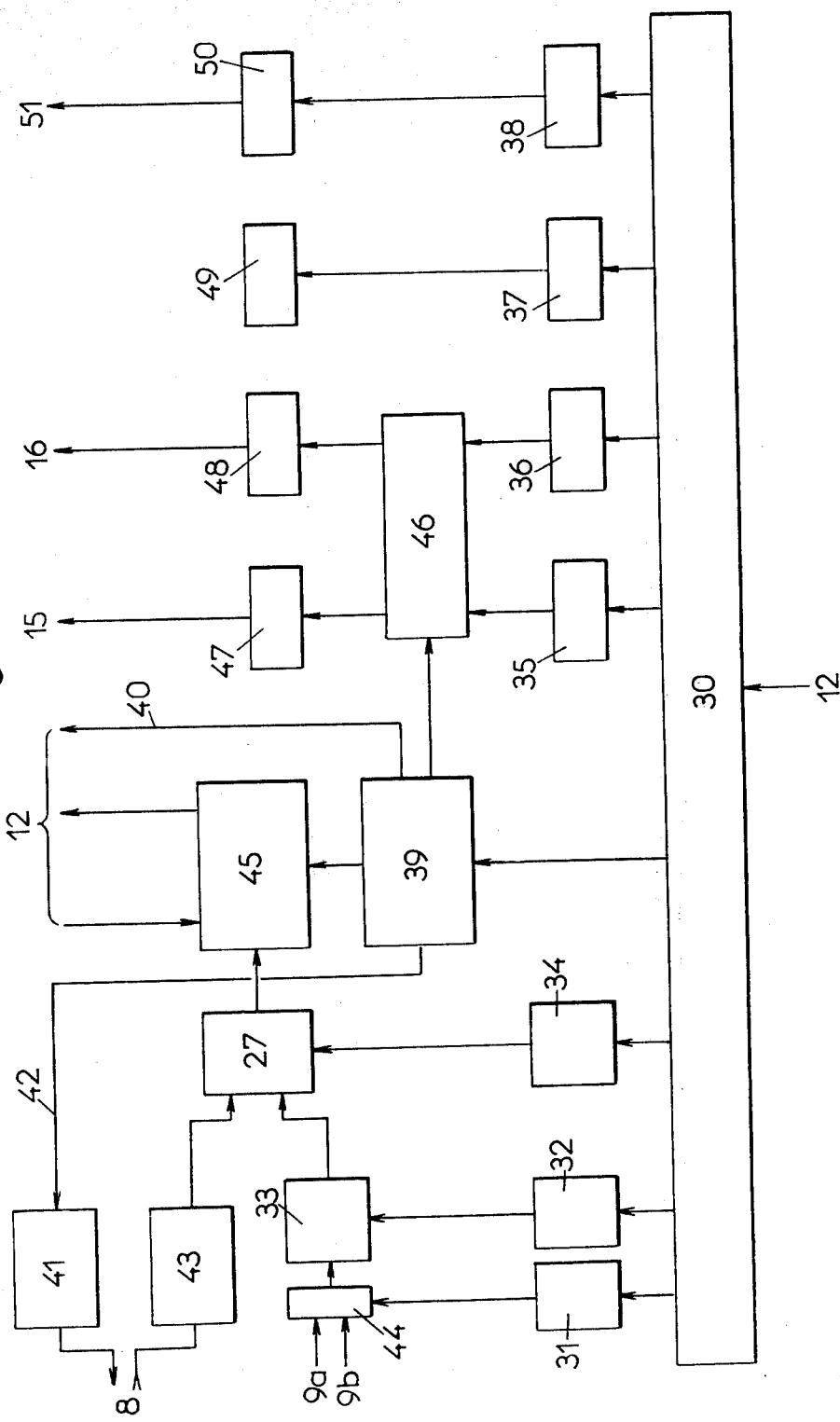

METHOD AND APPARATUS FOR THE CONTROL AND REGULATION OF GLYCEMIA

The invention is applicable to the supervision of diabetic patients dependent on insulin.

The present invention relates to the control and regulation of glycemia (that is the glucose rate in the blood) of diabetic patients.

It is known that the glucose rate in blood is normally one gram for human beings and that this rate is maintained in the vicinity of this value, in a healthy person, by an auto-regulation system comprising the liver, the pancreas, the hypophysis and other organs.

With diabetic patients, the glycemia is usually above 2 grams (hyper-glycemia) and this rate is reduced by means of insulin the effect of which is to reduce the glucose rate. However, said rate should not fall below 0.8 gram since in this case there would be a hypoglycemia.

It is therefore important to maintain the glycemia of diabetic patients depending on insulin at a value nearing 1 gram and preferably comprised between 0.8 and 1.2 g.

The device according to the invention aims actually at providing control and regulation of glycemia in order to maintain it in the vicinity of 1 g.

A device according to the invention is characterized in that it comprises, in combination, means for sampling continuously a very low blood flux from a diabetic patient, measuring means for determining continuously the glucose rate in said flux, electronic regulation means for comparing said rate so determined with the normal rate (of the order of 1 gram) and for determining the quantity of a product capable of reducing the glucose rate (such as insulin) or a product capable of raising such rate (such as glucose or glucagon) to be injected to the diabetic patient in order to bring back his glucose rate to the normal level, means for injecting effectively one or the other of said products, the last mentioned means being controlled by said regulation electronic means and eventually visualizing means for the glucose rate determined by said measuring means and/or alarm means capable of operating when the difference between said rate and the normal rate is in excess of a predetermined alarm threshold and/or when an operation anomaly occurs.

Preferably, the device comprises also means for determining the red cell concentration of the blood flux sampled from the patient.

In any case, the invention will become more apparent from the following description as well as from the accompanying drawings, said description and drawings being of course given mainly by way of examplification.

FIG. 4 finally shows in block-form the electronic unit receiving the measuring signals and controlling the injection, visualization and alarm means in cooperation with a computing unit.

Figure 1:
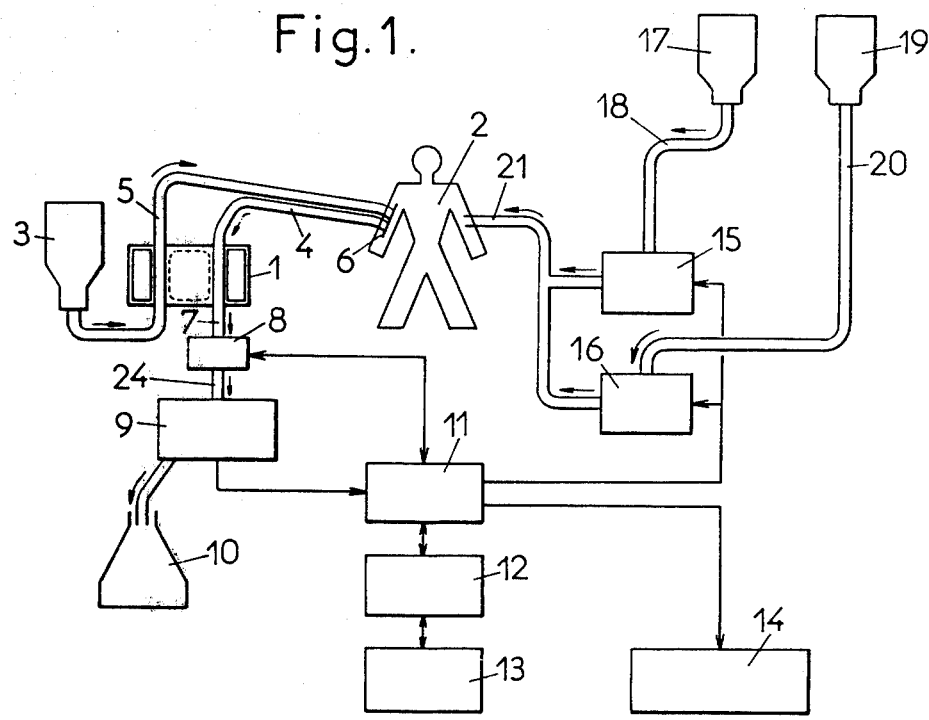
FIG. 1 shows schematically a device according to the invention controlling a diabetic patient.

The whole unit is illustrated in FIG. 1 in which the pipes transporting the liquids are represented in double lines with the flow direction indicated by arrows, whereas the electric leads carrying the information are shown in single lines, the arrows indicating the circulation direction of the electric data.

The total blood of a diabetic patient 2 depending on insulin is being sampled by means of a pump 1, for instance of the roller type. Pump 1 sucks also continuously a certain quantity of heparin contained in a container 3. In FIG. 1 is shown the pipe 5 for heparin and the pipe 4 for the total blood mixed with heparin on the level of the sampling catheter 6 which is of the double light type. The heparin is an anticoagulant substance, the presence of which in the blood avoids coagulation of the latter, which coagulation would result in the obstruction of the pipes and a distorsion of the measurements.

After pump 1, the heparin-containing total blood is transferred by a pipe 7 into a device 8 provided for measuring the red cell content and made for instance of an hematocrit electrode which will be described in more detail with reference to FIG. 2. Said electrode measures continuously the red cell content of the total blood and heparin mixture which should normally contain a constant proportion of heparin. However, when the elements of the device described so far and indicated by reference numerals 1, 3, 4, 5, 6 and 7 do not operate correctly, the heparin percentage could be modified, and this would lead to errors in the determination of the glycemia in unit 9 which is a glucose analyser. Since the cell concentration in blood is practically invariable in the human system over a long period, its determination in the hematocrit electrode 8 authorises detecting a modification of the heparin rate in the blood carried by pipe 7. In fact, if the heparin rate is constant, the quantity of red blood cells determined by electrode 8 should be constant. When there is a variation in this quantity of red cells, an anomaly has occured; said anomaly can be either a modification of the heparin rate, as hereabove mentioned, or the presence of air bubbles resulting in the formation of a blood clot or a leak in one of the pipes.

Downstream of the hematocrit electrode 8 is disposed, as previously mentioned, a glucose analyser 9 which will not be described in detail since it is of known type. It can operate either through the chemical and colorimetric route, or through the electro-chemical route. It could also be possible to determine the glucose rate in the blood mixed with heparin by using other properties such as for instance optic properties.

In any case, and whatever the type of the glucose analyser used, the latter emits an electric signal (voltage or current) which is a function of glycemia.

After passing through the glucose analyser 9, the blood mixed with heparin is collected in a vessel 10.

The signal from the glucose analyser 9, as well as the signal transmitted by the hematocrit electrode 8 which is a function of the quantity of red cells in the blood is transmitted to an electronic unit 11 which will be described hereafter with reference to FIG. 4 and which will be called hereafter glucostat since it represents the main element for the regulation of the glucose content in the blood of patient 2.

To glucostat 11 is associated a computing unit 12 which may be for instance a digital computing unit of the type manufactured and sold by the HEWLETT-PACKARD Company under number HP 9815 A, or a programmable computer or computing unit of equivalent or higher performance to that of the HP 9815 A.

The computing unit controls a printer 13 which prints the regulation important parameters: glucose content in the blood of patient 2, insulin rate injected to the patient, glucose or glucagon rate injected to the patient and eventually the quantity of red blood corpuscles. A further displaying means is constituted by a tracing table with several routes 14 operated by glucostat 11.

Said glucostat which comprises also an optic electronic display system for the glucose content in the blood of patient 2, controls the regulation of the glucose rate by actuating, according to the results from the glucose analyser 9, either of the two pumps 15 and 16. Pump 15 is provided for injecting insulin (thereby reducing the glucose rate) to patient 2 from an insulin container 17 via a pipe 18, whereas pump 16 is provided for injecting glucose (which of course is capable of increasing the blood glucose rate) to the patient from a glucose container 19 via a pipe 20, the insulin or glucose injection being made through a pipe 21. Glucagon may be used instead of glucose.

Briefly, if the quantity of red blood cells is normal, the glucostat 11 operates as follows:
(a) when the glucose analyser 9 indicates a normal glycemia, glucostat 11 acts only on the insulin pump 15 by sending to the patient a very low quantity of this hormone (in a quantity called basal quantity);
(b) when the glucose analyser 9 indicates a glycemia over the normal, glucostat 11 starts pump 15 which transfers insulin to the patient via pipes 18 and 21;
(c) when the glucose analyser 9 indicates a glycemia which is too low, glucostat 11 operates pump 16 for transferring to the patient glucose or glucagon via pipes 20 and 21.

The operation of glucostat 11 will be described in more detail with reference to FIG. 4.

Figure 2:
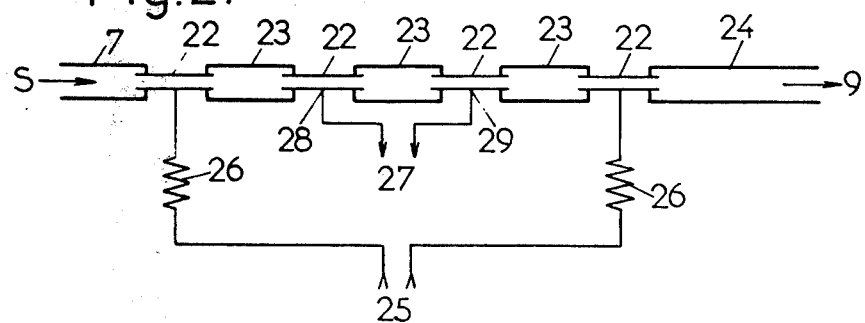
FIG. 2 illustrates one of the elements of the device of FIG. 1, namely the apparatus for determining the red cell concentration in the blood flux sampled from the diabetic patient.

Referring now to FIG. 2, an embodiment of an apparatus for determining the quantity of red cells in the blood and made of an hematocrit electrode will now be described.

The apparatus of FIG. 2 comprises a plurality of metallic pipes 22 arranged between plastic pipes of larger diameter 23, blood S mixed with heparin arriving from the left hand side via pipe 7 and flowing away on the right hand side via pipe 24 (also represented in FIG. 1) to the glucose analyser 9.

An input alternating voltage, for instance of 20 volts with a frequency of 500 Hertz, is applied at 25 between the two end metallic pipes across high ohmic value resistors 26 (with a rated value equal to or higher than 10 MΩ). The output signal which is a function of the quantity of red corpuscles in the blood flux S mixed with heparin is available at 27 and is sent to the glucostat 11. It will be noted that a symetrical arrangement is used in order to eliminate noises induced by radiation from the feed network connected at 25. Induced voltages more or less identical in amplitude and phase will thereby be obtained at 28 and 29. By providing a differential system at the output of 27, a resultant amplified voltage without component due to the network induction will be obtained.

The determination of the quantity of red cells is based on the following considerations:

If $\rho h$ is the impedance of a liquid with red blood corpuscles and $\rho sh$ the impedance of the same liquid without red blood cells, one has the equation:

$$\rho h = \rho sh \, (\gamma + H)/\gamma(1-h)$$

where $\gamma$ is a parameter depending on the shape of the red blood cells (which will be here considered as equal to 1.32) whereas h is the concentration of the red corpuscles (between 0.45 and 0.50 for blood).

If the resistances R are high relative to the resistance of the liquid, the circuit behaves as a steady current generator and $$V_z = V_0 \, (\gamma + h)/(\gamma(1-h))$$

where Vz is the voltage V measured in presence of blood and Vo the voltage V measured in presence of a physiological liquid without red cells.

The value of h will be obtained from this formula, and therefore the volumic percentage of the blood in the blood+ heparin mixture.

Figure 3:
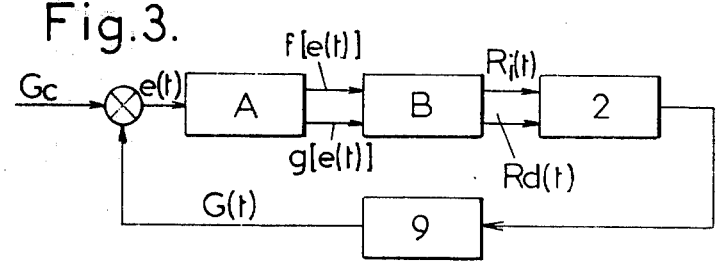
FIG. 3 illustrates schematically the regulation loop of the device of FIG. 1 which comprises said electronic regulation means.

In FIG. 3 has been illustrated schematically the regulation loop formed substantially by elements 9, 11, 12, 15 and 16 of FIG. 1. In this FIGURE has been shown by block A the assembly of elements 11 and 12 of FIG. 1, and by block B pumps 15 and 16 of FIG. 1; the patient is there again shown at 2 and the glucose analyser at 9.

In FIG. 3, the various electric signals have also been indicated, viz. those representing:
Gc:the desired value for the glycemia (rated point) from the computing device;
G(t):measured value of the glycemia from analyser 9;
e(t):value which is a function of the difference between Gc and G(t);
$R_i(t) = f[e(t)]$:insulin rate to be injected;
$R_d(t) = g[e(t)]$:glucose rate to be injected.

The servo-control of glycemia is provided entirely automatically. Due to a calculation and operation program, specially written to this effect, the computing device 12 determines values $f[e(t)]$ and $g[e(t)]$ from the measured value of glycemia. Functions f and g are empiric; they are based essentially on the observation of diabetes and of diabetic patients treated with insulin.

The program provides also control of the exchange of data between the computing device, some peripheral equipments and the glucostat.

Finally, there will be described with reference to FIG. 4 the glucostat 11 which provides a number of functions, viz.
the amplification, filtration and analog/digital (that is numeric) conversion of the electric data from the various captors (glucose analysers and hematocrit electrode);
the control of the pumps;
the control of the glycemia display;
the control of an alarm indicating an abnormal operation of the device.

The glucostat has a quartz time base used as clock for the whole system, manages the data exchanges with the computing unit and provides finally the supply in alternating current at 500 Hz of the hematocrit electrode (other frequencies could also be chosen).

Referring to FIG. 4, one sees that the glucostat comprises first a demultiplexor 30 directing towards the various units the data transmitted by the computing unit 12, said data being stored in the following units:
31, making the choice of the glucose analyser 9a, 9b;
32, making the gain choice of the differential amplifier 33;
34, making the choice of the type of measurement to be transmitted;
35, which stores the instructions for the insulin pump (shown at 15 in FIG. 1);

36 which stores the instructions for the glucose pump (shown at 16 in FIG. 1);

37, which stores the glycemia with a view to providing the display, and 38, which stores the eventual necessity of an alarm.

The glucostat comprises a time base 39 transmitting signals to a number of units, particularly to the computing device 12 via line 40 and to a generator 41 of sinusoidal voltage at 500 Hz through line 42, the time base 39 transmits rectangular signals at 500 Hz which are converted by generator 41 into a sinusoidal signal of same frequency). Said generator at 500 Hz supplies the hematocrit electrode 8 (at 25 in FIG. 2). Said electrode transmits its information signal to a differential amplifier 43 adjusted on 500 Hz and followed by a rectifier (not shown) supplying a continuous voltage from the 500 Hz signal from the hematocrit electrode, said voltage being applied to an analogous multiplexor 27 whose function will be explained hereafter.

In FIG. 4 has been considered the case where several analysers of different types for the glucose rate, viz. 9a and 9b, could be used. Unit 31 makes the choice of the analyser (9a or 9b) by means of an analogous multiplexor 44 which is also used as impedance matching device for each of the glucose analysors and which selects one of the signals from 9a and 9b in order to transmit it to the aforementioned differential amplifier 33 the gain of which is determined by unit 32 as a function of the analyser type for the glucose, said gain being determined by the computing unit 12.

The analogous multiplexor 27 choses, under the control of unit 34, the glycemia signal, (from 33) or the red cell quantity signal (from 43) to be fed to the analog/digital converter 45 which is connected bi-directionally to the computing unit 12 to which it feeds a signal indicating either the glucose rate or the red cell quantity of the blood mixed with heparin. As a function of the glucose rate and possibly of the red cell quantity, the computing unit controls, through the demultiplexor 30 and the storage units 35 and 36, unit 46 providing control of the insulin and glucose pumps 15 and 16 respectively, through power circuits 47 and 48 respectively. The type of information transmitted by the computing unit 12 to unit 46 and from there to units 47 and 48 depends on the nature of the pumps 15 and 16 which are used: in the case of roller pumps, the signal represents the duration of the operation per time unit or the rotation speed of the pump, whereas for impulse pumps, the signal represents the number of strokes per minute.

Finally, the storing units 37 and 38 act respectively on a digital display device 49 and on a power amplifier 50 emitting through a loud-speaker positioned at 51 and transmitting an audible signal when the alarm threshold for the glucose concentration of the blood of patient 2 is exceeded and in the case where an anomaly is detected (it may be an incorrect red cell rate or a variation of the glycemia which is not physiologically compatible).

A device is thereby realized which provides a very efficient control and regulation of the glycemiaa for diabetic patients dependent on insulin.

With such a device, one can maintain said glycemia between 0.8 and 1.2 grams, which is very satisfactory.

The operation of the device according to the invention is completely automatic and requires no continuous supervision since it supplies on the one hand a continuous record of the glycemia and on the other hand an audible signal when a dangerous threshold for the glycemia is exceeded, viz. when the difference e(t) between the value measured for the glycemia G(t) and the desired value for the glycemia Gc exceeds a predetermined alarm threshold and/or a loud signal when there is an abnormal operation.

Instead of an audible signal, one could foresee a luminous alarm signal, but such a signal requires a more careful supervision although it is possible to concentrate in a single room the alarm luminous signals from many devices according to the invention which control several diabetic patients.

I claim:

1. A control and regulation system for continuously monitoring glycemia for a diabetic patient, comprising, in combination, means for continuously withdrawing and sampling a low flux of the blood of the diabetic patient, measuring means for continuously determining the glucose concentration in said flux, electronic regulation means for determining the difference between the concentration thus determined and the normal concentration and for determining the quantity of product capable of adjusting the glucose concentration to the normal concentration; means for injecting the diabetic patient with a suitable amount of glucose or insulin to produce said normal concentration, the amount of such injection being controlled by said electronic regulation means, and being a function of said difference.

2. A system according to claim 1, which comprises also means for determining the red cell concentration of the blood flux sampled from the patient, and means for correcting the glucose concentration responsive to said red cell concentration.

3. A system according to claim 2, wherein said a means for determining the red cell concentration is constituted by a hematocrit electrode comprising four metallic tubes arranged in series between plastic tubes, means for applying an alternating voltage between the two end metallic tubes and means for taking up an output voltage between the inner tubes, said voltage being representative of the red corpuscle concentration.

4. A system according to claim 1, wherein said regulation electronic means comprise, in combination with a computing unit, a demultiplexor capable of transmitting selectively the signals from the computing unit, a series of storing units receiving the signals from the computing unit through said demultiplexor, and an analog/digital converter, means for selectively transmitting the output signal from said measuring means for determining the glucose rate, and eventually means for determining the red corpuscle concentration, on said analog/digital converter, said analog/digital converter being in bi-directional relation with the computing unit, a time base capable of controlling the timing of the various operations, a sinusoidal voltage generator for said hematocrit electrode, means for controlling said means for injecting effectively one or the other of the products and eventually control means for a visualization device of the glucose rate and/or alarm means, and particularly sound means.

5. A method for controlling blood glucose levels comprising the steps of:
    (1) withdrawing and continuously sampling a low flux of blood from the diabetic patient,
    (2) continuously measuring the glucose concentration in said flux,
    (3) electronically determining the difference between said glucose concentration and the normal glucose concentration for determining the quantity of glucose or insulin necessary to adjust the glucose concentration to the normal concentration, and (4) injecting the diabetic patient with a suitable quantity of glucose or insulin determined by said electronic comparison, said quantity being a function of said difference.

6. The method of claim 5, further comprising the step of determining the red cell concentration of the blood sample and correcting the determined glucose rate responsive to said red cell concentration.

* * * * *